(12) United States Patent
Wada

(10) Patent No.: US 10,383,774 B2
(45) Date of Patent: *Aug. 20, 2019

(54) DEVICE FOR PRODUCING DISPOSABLE WEARABLE ARTICLE AND METHOD FOR PRODUCING DISPOSABLE WEARABLE ARTICLE

(71) Applicant: ZUIKO CORPORATION, Osaka (JP)

(72) Inventor: Takao Wada, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 509 days.

This patent is subject to a terminal disclaimer.

(21) Appl. No.: 15/022,246

(22) PCT Filed: Sep. 22, 2014

(86) PCT No.: PCT/JP2014/075112

§ 371 (c)(1),
(2) Date: Mar. 16, 2016

(87) PCT Pub. No.: WO2015/046157

PCT Pub. Date: Apr. 2, 2015

(65) Prior Publication Data

US 2016/0228303 A1    Aug. 11, 2016

(30) Foreign Application Priority Data

Sep. 30, 2013   (JP) ................................ 2013-203040
Sep. 30, 2013   (JP) ................................ 2013-203041
Sep. 30, 2013   (JP) ................................ 2013-203042

(51) Int. Cl.
*A61F 13/15*      (2006.01)
*B65H 23/32*     (2006.01)
(Continued)

(52) U.S. Cl.
CPC .. *A61F 13/15764* (2013.01); *A61F 13/15739* (2013.01); *A61F 13/15747* (2013.01);
(Continued)

(58) Field of Classification Search
CPC .......... A61F 13/15764; A61F 13/15747; A61F 13/15739; A61F 13/15772;
(Continued)

(56) References Cited

U.S. PATENT DOCUMENTS 5,879,500 A  *  3/1999  Herrin ............... A61F 13/15804
                                                        156/163
6,234,229 B1 *  5/2001  Tabuchi ............ A61F 13/15747
                                                        156/289

(Continued)

FOREIGN PATENT DOCUMENTS

CN          1386481        12/2002
CN         100475675        4/2009
(Continued)

OTHER PUBLICATIONS

European Search Report dated Aug. 24, 2016.
(Continued)

*Primary Examiner* — Michael N Orlando
*Assistant Examiner* — Christian Roldan
(74) *Attorney, Agent, or Firm* — Gerald E. Hespos; Michael J. Porco; Matthew T. Hespos

(57) ABSTRACT

Provided are a device for producing a disposable wearable article and a method for producing a disposable wearable article capable of suppressing the occurrence of a sealing failure by making it difficult for a doubled sheet to open against an elastic force of an absorber. A device for producing a disposable wearable article includes a jointing/cutting unit (60) provided in a line (L1) for continuously conveying a sheet (W) and configured to join parts of the doubled sheet
(Continued)

(W) at opposite sides of an absorber (C) and then cut the joined parts and a pressing unit (70) arranged upstream of the jointing/cutting unit (60) in a conveying direction (a). The pressing unit (70) includes a pressing mechanism (71, 72) configured to press the sheet (W) together with the absorber (C) in a thickness direction.

10 Claims, 9 Drawing Sheets

(51) Int. Cl.
  *B65H 45/22*    (2006.01)
  *B31F 1/00*    (2006.01)
(52) U.S. Cl.
  CPC .. *A61F 13/15772* (2013.01); *A61F 13/15804* (2013.01); *B65H 23/32* (2013.01); *B65H 45/22* (2013.01); *A61F 2013/15861* (2013.01); *B31F 1/00* (2013.01); *B65H 2301/33212* (2013.01); *B65H 2301/33222* (2013.01); *B65H 2404/2614* (2013.01); *B65H 2701/1123* (2013.01); *B65H 2701/1942* (2013.01); *B65H 2801/57* (2013.01)
(58) Field of Classification Search
  CPC ..... A61F 13/15804; A61F 2013/15861; B65H 45/22; B65H 23/32; B65H 2301/33222; B65H 2301/33212; B65H 2701/1942; B65H 2404/2614; B65H 2701/1123; B65H 2801/57; B31F 1/00
  USPC ......................................................... 156/250
  See application file for complete search history.

(56) References Cited

U.S. PATENT DOCUMENTS

| | | | |
|---|---|---|---|
| 6,546,987 | B1 | 4/2003 | Tachibana et al. |
| 6,685,613 | B1 | 2/2004 | Stopher et al. |
| 7,144,357 | B2* | 12/2006 | Yamamoto ........ A61F 13/15747 493/34 |
| 9,168,183 | B2* | 10/2015 | Yamamoto ........ A61F 13/15747 |
| 2002/0174930 | A1* | 11/2002 | Umebayashi ..... A61F 13/15764 156/62.6 |
| 2004/0075052 | A1 | 4/2004 | Shirai |
| 2004/0123954 | A1* | 7/2004 | Yoneoka ........... A61F 13/15593 156/494 |
| 2005/0189063 | A1 | 9/2005 | Mizutani et al. |
| 2006/0196594 | A1* | 9/2006 | Shimizu ........... A61F 13/15747 156/64 |
| 2008/0081123 | A1* | 4/2008 | Swanson ................. B05D 3/12 427/496 |
| 2009/0266491 | A1 | 10/2009 | Mizutani et al. |
| 2010/0050411 | A1* | 3/2010 | Yamamoto ........ A61F 13/15747 29/428 |
| 2010/0179042 | A1* | 7/2010 | Yamamoto ........ A61F 13/15747 493/379 |
| 2011/0277921 | A1 | 11/2011 | Ogasawara et al. |
| 2013/0019733 | A1 | 1/2013 | Yamamoto |
| 2013/0156536 | A1 | 6/2013 | Dowiasch et al. |
| 2013/0270068 | A1 | 10/2013 | Murakami et al. |

FOREIGN PATENT DOCUMENTS

| | | |
|---|---|---|
| CN | 102341078 | 2/2012 |
| CN | 202367791 | 8/2012 |
| CN | 102695486 | 9/2012 |
| CN | 103124546 | 5/2013 |
| CN | 103987350 | 8/2014 |
| EP | 140778 A2 | 4/2004 |
| EP | 1410778 A2 | 4/2004 |
| JP | H0640203 Y2 | 10/1994 |
| JP | H10119459 A | 5/1998 |
| JP | 2000-25518 | 9/2000 |
| JP | 2000-255518 | 9/2000 |
| JP | 2003-038566 | 2/2003 |
| JP | 2004141626 A | 5/2004 |
| JP | 2007-125407 | 5/2007 |
| JP | 2010-142417 | 7/2010 |
| JP | 2010-227545 | 10/2010 |

OTHER PUBLICATIONS

Japanese Office Action dated Feb. 21, 2017.
International Search Report.
Opinion of Appealer Against Chinese Utility Model Appl. No. 201320617773.5.
Opinion of Appealer Against Chinese Utility Model Appl. No. 201320617774.X.
Opinion of Appealer Against Chinese Utility Model Appl. No. 201320618301.1.

* cited by examiner

DEVICE FOR PRODUCING DISPOSABLE WEARABLE ARTICLE AND METHOD FOR PRODUCING DISPOSABLE WEARABLE ARTICLE

TECHNICAL FIELD

The present invention relates to a device and a method for producing a disposable wearable article.

BACKGROUND ART

Conventionally, a device provided with an absorber arranging unit 10, an elastic attaching unit 20, a hole forming unit 30 and a doubling unit 40, a twisting unit 50 and a joining/cutting unit 60 in a line for continuously conveying a sheet W in a horizontal direction (direction to make a sheet width direction horizontal) as shown in FIG. 10 is known as a device for producing a disposable wearable article (see Publication of Japanese Patent No. 3910478).

In the absorber arranging unit 10, absorbers C are arranged at a predetermined interval on a surface of the sheet W from a drum 11. In the elastic attaching unit 20, at least one(s) of a waist elastic F and leg elastics for leg gather is/are attached to the surface of the sheet W. In the hole forming unit 30, holes H, which will serve as leg holes, are perforated at opposite sides of the absorber C in a conveying direction of the sheet W. In this way, a part of the sheet W having the absorber C arranged thereon functions as a crotch part.

In the doubling unit 40, the sheet W is doubled together with the absorber C in a vertical direction (direction perpendicular to the sheet width direction) such that opposite side edges W1, W2 of the sheet W are proximate to or overlapped with each other.

In the twisting unit 50, the doubled sheet is returned to a horizontal orientation by being twisted 90° while being guided using a plurality of guiding bars 51.

In the joining/cutting unit 60, after parts of the doubled sheet W at the opposite sides of the absorber C (opposite sides of a waist part) are joined on a drum 61, these joined parts are cut. In this way, a pants-type disposable wearable article P is separated from the sheet W. Note that, in FIG. 10, the posture of the separated disposable wearable article P is turned 90° on the line.

In the device for producing a disposable wearable article as described above, the crotch part is pressed against a bottom edge of a doubling member 41 in the doubling unit 40. This causes the opposite side edges W1, W2 of the sheet W to vertically stand together with the absorber C and this sheet W is doubled.

However, if the doubled sheet is opened by an elastic force of the absorber, the sheet on one side, which will become a front belly part, and the sheet on the other side, which will become a back part, are not held in a state of adhesion in the joined (sealed) parts at the opposite sides of the absorber later in the joining/cutting unit. This causes a problem of causing a sealing failure.

SUMMARY OF INVENTION

The present invention aims to provide a device for producing a disposable wearable article and a method for producing a disposable wearable article capable of suppressing the occurrence of a sealing failure by making a doubled sheet difficult to open against an elastic force of an absorber.

To solve the above problem, the present invention provides a device for producing a disposable wearable article, the device including a doubling unit provided in a line for continuously conveying a sheet and configured to double the sheet together with an absorber such that opposite side edges of the sheet having the absorber arranged thereon are proximate to or overlapped with each other, a joining/cutting unit provided in the line and configured to join parts of the doubled sheet at opposite sides of the absorber and then cut the joined parts, and a pressing unit arranged upstream of the joining/cutting unit in a sheet conveying direction, the pressing unit including a pressing mechanism configured to press the doubled sheet together with the absorber in a thickness direction.

Further, the present invention provides a method for producing a disposable wearable article, the method including a conveying process of continuously conveying a sheet, an absorber arranging process of arranging an absorber on a surface of the sheet, a doubling process of doubling the sheet together with the absorber such that opposite side edges of the sheet having the absorber arranged thereon are proximate to or overlapped with each other, a jointing/cutting process of joining parts of the doubled sheet at opposite sides of the absorber and then cutting the joined parts, and a pressing process of pressing the doubled sheet together with the absorber prior to the jointing/cutting process.

According to the present invention, it is possible to suppress the occurrence of a sealing failure by making a doubled sheet difficult to open against an elastic force of an absorber.

DESCRIPTION OF EMBODIMENT

Hereinafter, an embodiment of the present invention is described in detail with reference to the drawings.

Figure 9:
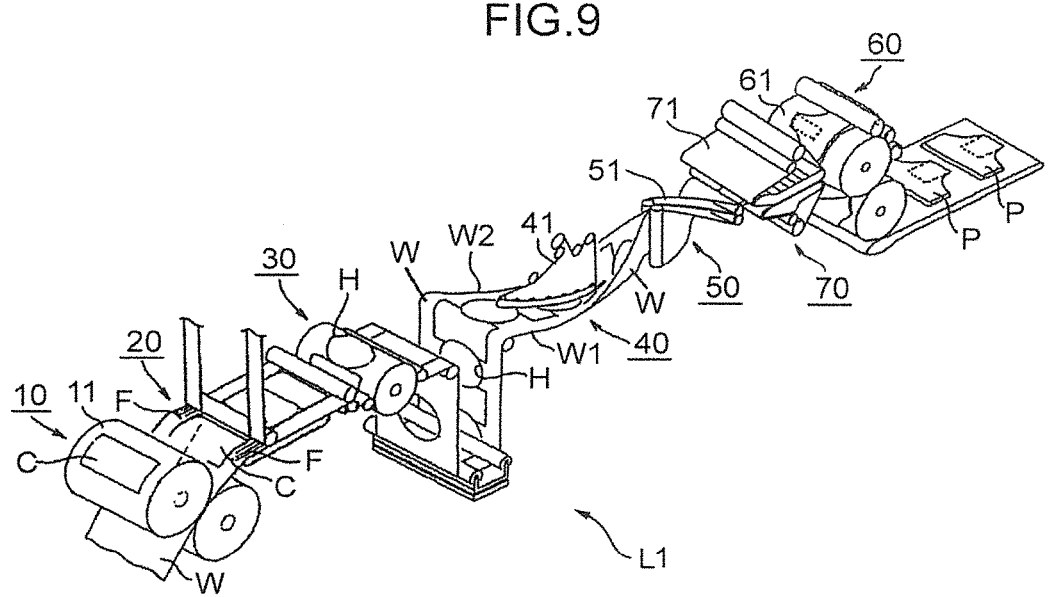
FIG. 9 is a perspective view of the device for producing a disposable wearable article according to the present invention.

A device for producing a disposable wearable article according to the present invention includes a line L1 for continuously conveying a sheet W in a horizontal direction (direction to make a width direction of the sheet W horizontal; the same holds true below) as shown in FIG. 9.

Further, the device for producing a disposable wearable article includes an absorber arranging unit 10, an elastic attaching unit 20, a hole forming unit 30, a doubling unit 40, a twisting unit 50, a joining/cutting unit 60 and a pressing unit 70 provided in the line L1.

The absorber arranging unit 10 intermittently arranges the absorbers C on a surface of the sheet W. The elastic attaching unit 20 attaches a waist elastic F to the surface of the sheet W. The hole forming unit 30 forms holes H, which will serve as leg holes, on the sheet W. The doubling unit 40 doubles the sheet W in a vertical direction (direction perpendicular to the width direction of the sheet W; the same holds true below) such that opposite side edges W1, W2 of the sheet W are proximate to or overlapped with each other. The twisting unit 50 returns the doubled sheet W to a horizontal orientation. The joining/cutting unit 60 joins parts of the doubled sheet W at opposite sides of the absorber C (opposite parts of a waist part) and, then, cuts these joined parts.

Although the absorbers C are directly arranged on the sheet W by the drum 11 and the like in the absorber arranging unit 10 here, the absorbers C may be arranged on another sheet and, thereafter, this other sheet may be placed on the sheet W.

Although the waist elastic F is attached to the sheet W having the absorber C arranged thereon in the elastic attaching unit 20, the waist elastic F may be attached between another sheet and the sheet W. Further, if leg elastics for leg gather are attached to the sheet W before the absorber C is arranged, the waist elastic F may be attached onto the sheet W when the leg elastics are introduced.

In the hole forming unit 30, the holes H, which will become leg holes, are perforated at a predetermined interval on the sheet W having the waist elastic F attached thereto by an unillustrated leg hole cutter. Members cut out from the sheet W are discharged to the outside of a production line system by unillustrated vacuum. In this way, a part of the sheet W between the holes H becomes the crotch part. Note that the holes H, which will become leg holes, may be perforated before the waist elastic F is introduced or before the absorber C is arranged.

After the holes H are perforated on the sheet W and the waist elastic F is arranged, the sheet W is introduced to the doubling unit 40. The bottom edge of a doubling member 41 of the doubling unit 40 comes into contact with a substantially center of the sheet W in the width direction, and the sheet W is doubled together with the absorber C such that the first side edge W1 and the second side edge W2 thereof are matched. The position of the doubling member 41 may be adjustable in the vertical and lateral directions. Note that a specific configuration of the doubling unit 40 is described later.

The doubled sheet W is returned to the horizontal orientation by being twisted 90° by the twisting (twist) unit 50. Specifically, the sheet W is doubled in the vertical direction along a substantially vertical plane in the doubling unit 40. To facilitate sealing in a later process, the sheet W is returned to the horizontal orientation along a substantially horizontal plane by the twisting unit 50 and conveyed in this state. Note that a specific configuration of the twisting unit 50 is described later.

The sheet W twisted by the twisting unit 50 is sealed on a drum 61 of the joining/cutting unit 60. The sheet W may be sealed, for example, by a heat-seal method disclosed in Japanese Unexamined Patent Publication No. 2000-255518 or may be sealed by ultrasonic welding. By sealing, adjacent disposable wearable articles P are partitioned from each other. The wearable articles P partitioned by sealing are cut by an unillustrated cutter to separate the wearable articles P from the sheet W.

Note that the posture of the wearable article P may be turned 90° and an interval between adjacent wearable articles P may be changed if necessary. For example, the wearable articles P may be placed on a pad moving above the drum and the posture of the pad may be turned 90° or the interval of the wearable articles P may be changed by changing a speed of the pad.

The pressing unit 70 (see FIG. 9) is provided before the joining/cutting unit 60. Note that a specific configuration of the pressing unit 70 is described later.

The specific configurations of the doubling unit 40, the twisting (twist) unit 60 and the pressing unit 70 are successively described below.

Figure 1:
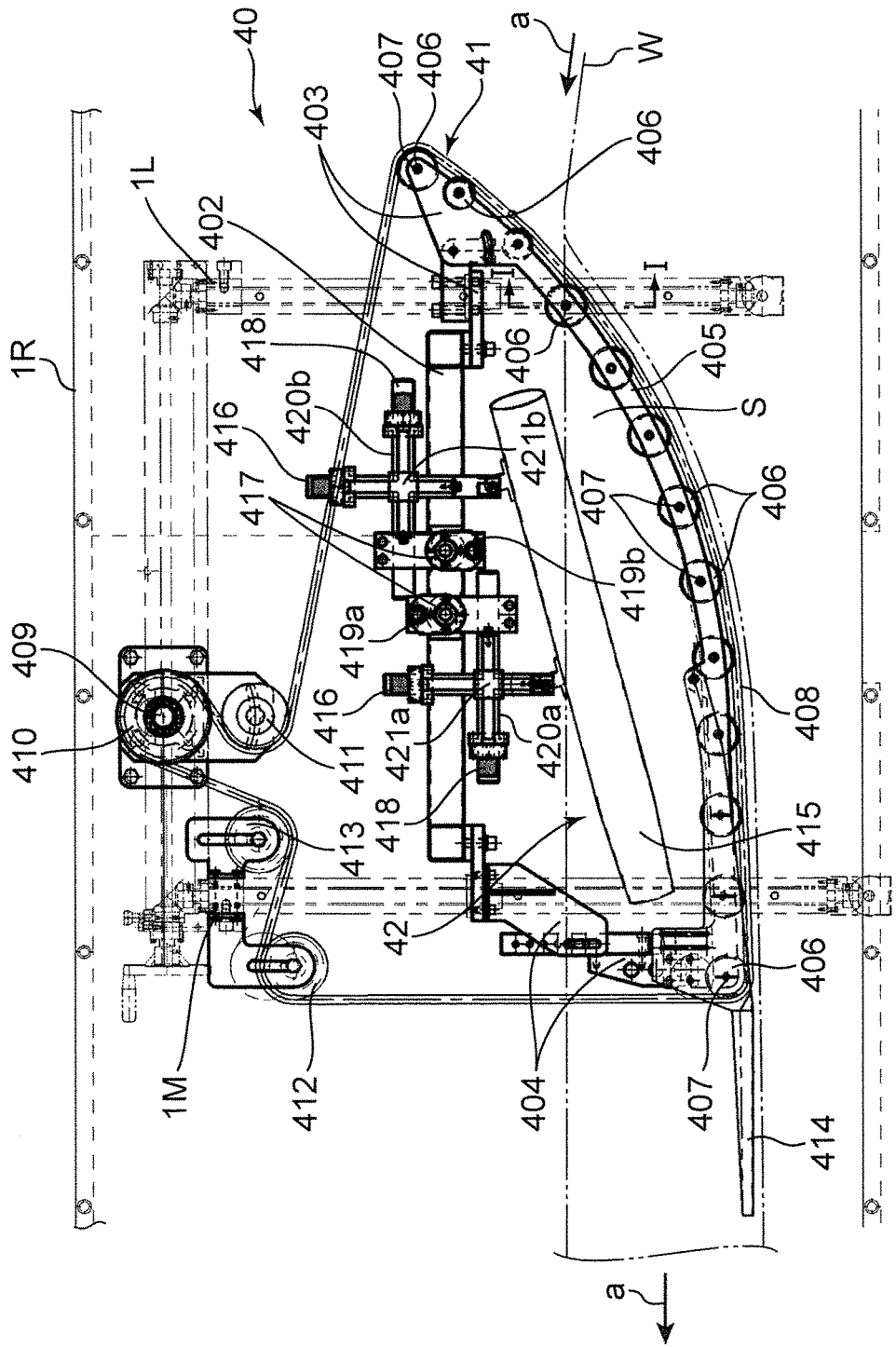
FIG. 1 is a side view of a doubling unit in a device for producing a disposable wearable article according to the present invention.

First, the specific configuration of the doubling unit 40 is descried. FIG. 1 is a side view of the doubling unit 40 and FIG. 2 is a plan view of FIG. 1.

Figure 2:
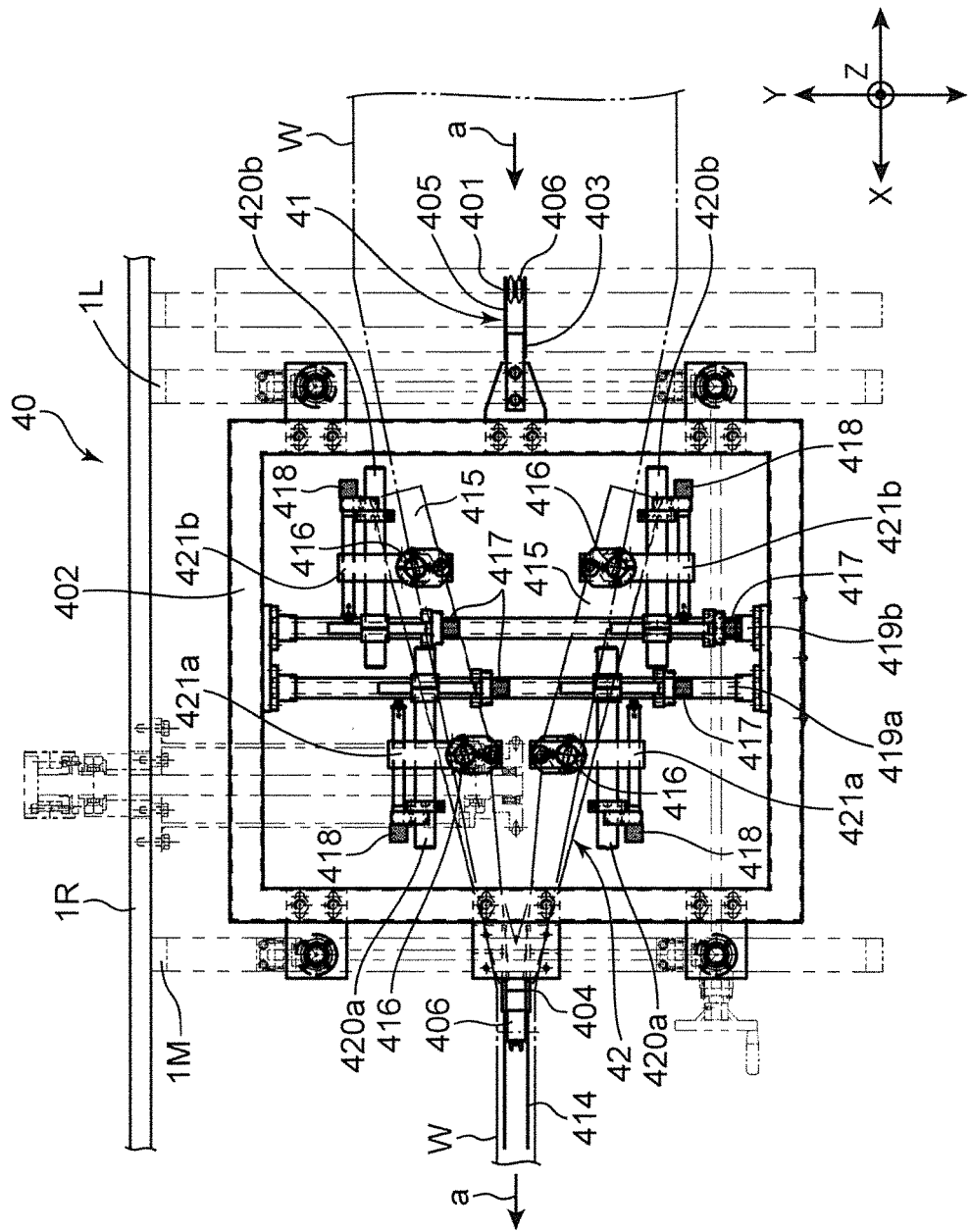
FIG. 2 is a plan view of the doubling unit of FIG. 1.

In FIGS. 1 and 2, the sheet W is continuously conveyed in a horizontal orientation from right to left.

The doubling unit 40 includes a front frame 1L and a rear frame 1M provided on a main supporting wall 1R standing along the line L1 for the sheet W, and a unit frame 402 mounted on the main supporting wall 1R via the frames 1L, 1M. The unit frame 402 is shaped into a rectangular frame in the plan view of FIG. 2.

Further, the doubling unit 40 includes the doubling member 41 mounted on the unit frame 402 and having the bottom edge for doubling the sheet W by coming into contact with a substantially center of the sheet W in the width direction.

The bottom edge of the doubling member 41 is so shaped that an arcuate part on a carry-in side of the sheet W and a substantially horizontal part on a carry-out side are continuous in the side view of FIG. 1. A plurality of front brackets 403 projecting forward are mounted on a front end part of the unit frame 402 on the carry-in side, and a plurality of rear brackets 404 projecting downward are mounted on a rear end part of the unit frame 402 on the carry-out side.

The doubling member 41 includes a pair of left and right plates 405.

These plates 405 are provided between the leading ends of the front brackets 403 and the lower ends of the rear brackets 404 and are so shaped that an arcuate part and a substantially horizontal part are continuous in the side view of FIG. 1.

Figure 3:
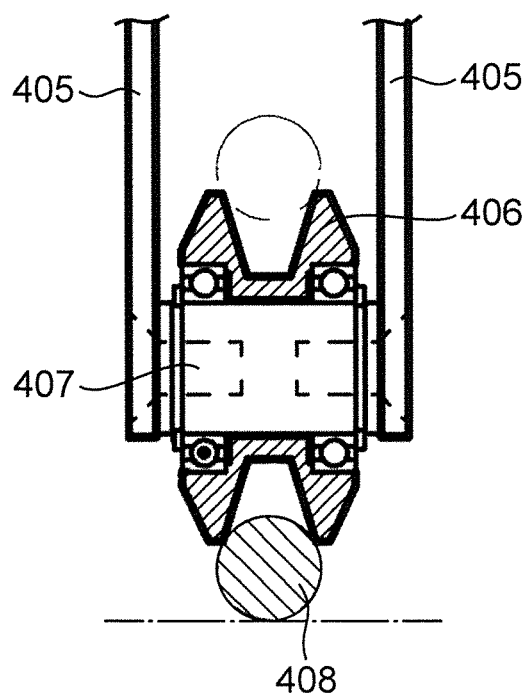
FIG. 3 is a sectional view along line I-I of FIG. 1.

Further, the doubling member 41 includes a plurality of (thirteen in this example) pulleys (friction reducing mechanism) 406 arranged at a predetermined distance in the conveying direction a of the sheet W between the pair of left and right plates 405. Each pulley 406 is mounted on a pulley shaft 407 provided between the both plates 405 to be freely rotatable about the pulley shaft 407. As shown in FIG. 3, any of the pulleys 406 has a cross-sectional shape with a recessed central part.

An electric motor (folding motor) 409, an output pulley 410 and a guide pulley 411 of this electric motor 409 are arranged above the unit frame 402. Further, a plurality of tension pulleys 412, 413 are mounted on the rear frame 1M. Any of the pulleys 410 to 413 has a cross-sectional shape with a recessed central part.

The doubling member 41 includes a folding endless belt (friction reducing mechanism) 408 having a circular cross-section (see FIG. 3). The folding endless belt 408 is continuously mounted on the pulleys 406, 410 to 413 while being inserted in the recesses of the respective pulleys 406, 410 to 413. By driving the electric motor 409, the folding endless belt 408 arranged on a bottom edge side of the doubling member 41 moves along the conveying direction a (see arrows of FIG. 1) of the sheet W.

The folding endless belt 408 and the pulleys 406 are provided on the bottom edge of the doubling member 41 and correspond to a friction reducing mechanism for reducing friction between the doubling member 41 and the crotch part of the sheet W in a state held in contact with the crotch part of the sheet W including the absorber C.

That is, the friction reducing mechanism includes the pulleys 406 rotatably provided on the bottom edge of the doubling member 41 and the folding endless belt 408 mounted on each pulley. The plurality of pulleys 406 hold the folding endless belt 408 such that a part of the folding endless belt 408 held in contact with the crotch part is movable in the conveying direction a.

Further, the friction reducing mechanism further includes the electric motor 409 for driving the folding endless belt 408 such that a moving speed of the part of the folding endless belt 408 held in contact with the crotch part and a conveying speed of the sheet W are substantially equal.

In FIG. 1, the sheet W is conveyed in the horizontal orientation to the vicinity of the pulley 406 at a predetermined position. A part of the folding endless belt 408 mounted on the pulley 406 is so shaped that an arcuate part extending downward and a part extending substantially horizontally from this arcuate part are continuous. Accordingly, by the contact of the parts of the folding endless belt 408 mounted on the pulleys 406 with the sheet W, the sheet W is doubled to be in a vertical orientation together with the absorber C such that the opposite side edges of the sheet W having the absorber C arranged thereon are proximate to or overlapped with each other. Note that a guide 414 projecting backward from the pair of left and right plates 405 to guide the doubled sheet W is provided on rear parts of the both plates 405.

In a side view, a space S is formed in a side surface part of the doubling member 41, i.e. a part enclosed by the unit frame 402, the front bracket 403, the rear bracket 404 and the plates 405. A posture adjusting mechanism 42 capable of adjusting the posture of the sheet W by coming into contact with an inner surface (surface whose halves to be doubled face each other; the same holds true below) of the sheet W being doubled is provided in this space S.

The posture adjusting mechanism 42 includes a pair of left and right bar-like guides 415 which come into contact with the inner surface of the sheet W being doubled, and a guide supporting mechanism (denoted by no reference sign) which supports these guides 415.

The both guides 415 are arranged in a V shape open toward the carry-in side of the conveying direction a in the plan view of FIG. 2 and inclined downwardly toward the carry-out side of the conveying direction a in the side view of FIG. 1.

In FIG. 2, the guide supporting mechanism is described, assuming a direction parallel to the conveying direction a as an X direction, a direction perpendicular to the conveying direction a as a Y direction and a direction perpendicular to the X and Y directions as a Z direction.

The guide supporting mechanism includes a pair of main shafts 419*a*, 419*b* mounted on the unit frame 402 while extending in the Y direction and being arranged side by side in the X direction, a pair of Y supporting shafts 420*a* mounted on the main shaft 419*a* movably in the Y direction, a pair of Y supporting shafts 420*b* mounted on the main shaft 419*b* movably in the Y direction, a pair of X supporting shafts 421*a* mounted on the respective Y supporting shafts 420*a* movably in the X direction and a pair of X supporting shafts 421*b* mounted on the respective Y supporting shafts 420*b* movably in the X direction.

Further, the guide supporting mechanism includes four Y-axis ball screws 417 threadably engaged with the respective Y supporting shafts 420*a*, 420*b* and adapted to allow movements of the respective Y supporting shafts 420*a*, 420*b* relative to the main shaft 419*a* in the Y direction, four X-axis ball screws 418 threadably engaged with the respective X supporting shafts 421*a*, 421*b* and adapted to allow movements of the respective X supporting shafts 420*a*, 420*b* relative to the respective Y supporting shafts 420*a*, 420*b* in the X direction, and four Z-axis ball screws 416 threadably engaged with the respective X supporting shafts 421*a*, 421*b* while penetrating through the respective X supporting shafts 421*a*, 421*b* in the Z direction.

One of the guides 415 is mounted on the lower ends of two Z-axis ball screws 416 arranged side by side in the X direction on one side in the Y direction, and the other of the guides 415 is mounted on the lower ends of two Z-axis ball screws 416 arranged side by side in the X direction on the other side in the Y direction. The two Z-axis ball screws 416 arranged in the X direction are mounted at positions of the guide 415 different in the X direction.

Accordingly, the position of each guide 415 in the Z direction and an angle of inclination of each guide 415 in the Z direction can be finely adjusted by changing tightening degrees of the Z-axis ball screws 416.

Further, the positions of the guides 415 on an X-Y plane and the angles of inclination of the guides 415 can be finely adjusted by changing tightening degrees of the Y-axis ball screws 417 and the X-axis ball screws 418.

According to the doubling unit 40, the friction reducing mechanism is provided on the bottom edge of the doubling member 41 of the doubling unit 40. In this way, friction between the bottom edge of the doubling member 41 and the crotch part of the sheet W can be reduced.

Specifically, the folding endless belt 408 is continuously mounted on the pulleys 406, 410 to 413. Since this enables the part of the folding endless belt 408 held in contact with the crotch part to lightly move in the conveying direction a of the sheet W, friction between the bottom edge of the doubling member 41 and the crotch part is reduced.

Accordingly, a reduction of the conveying speed of the crotch part with respect to the conveying speed of a part (waist part) of the sheet W other than the crotch part can be suppressed. Thus, the sheet W can be conveyed at a high speed to the next process while being kept in a normal shape without distorting the shape of the sheet W in the conveying direction a. As a result, the occurrence of a trouble in a processing work in the next process following the doubling process can be suppressed.

Further, the folding endless belt 408 is provided as the friction reducing mechanism and moved in the conveying direction a by the electric motor 409, whereby the folding endless belt 408 moves substantially at the same speed as the conveying speed of the sheet W. Thus, friction between the folding endless belt 408 and the crotch part can be completely or mostly eliminated.

Note that the friction reducing mechanism is not limited to that of the above embodiment. Instead of the friction reducing mechanism of the above embodiment, an arrangement of a plurality of rollers may be used as the friction reducing mechanism. Further, the folding endless belt 408 needs not be necessarily moved in the conveying direction a by the electric motor 409.

Further, since the posture of the sheet W can be adjusted by the posture adjusting mechanism 42, the posture of the sheet W can be easily and quickly finely adjusted unlike a conventional doubling member formed of a metal plate material with which the posture of the sheet W cannot be adjusted unless the doubling member is exchanged.

Further, unlike a case where the sheet W is suddenly doubled in the conveying direction a, the sheet W can be gradually doubled by the posture adjusting mechanism 42, wherefore tension generated on an edge part of the sheet W in the width direction can be alleviated.

Figure 4:
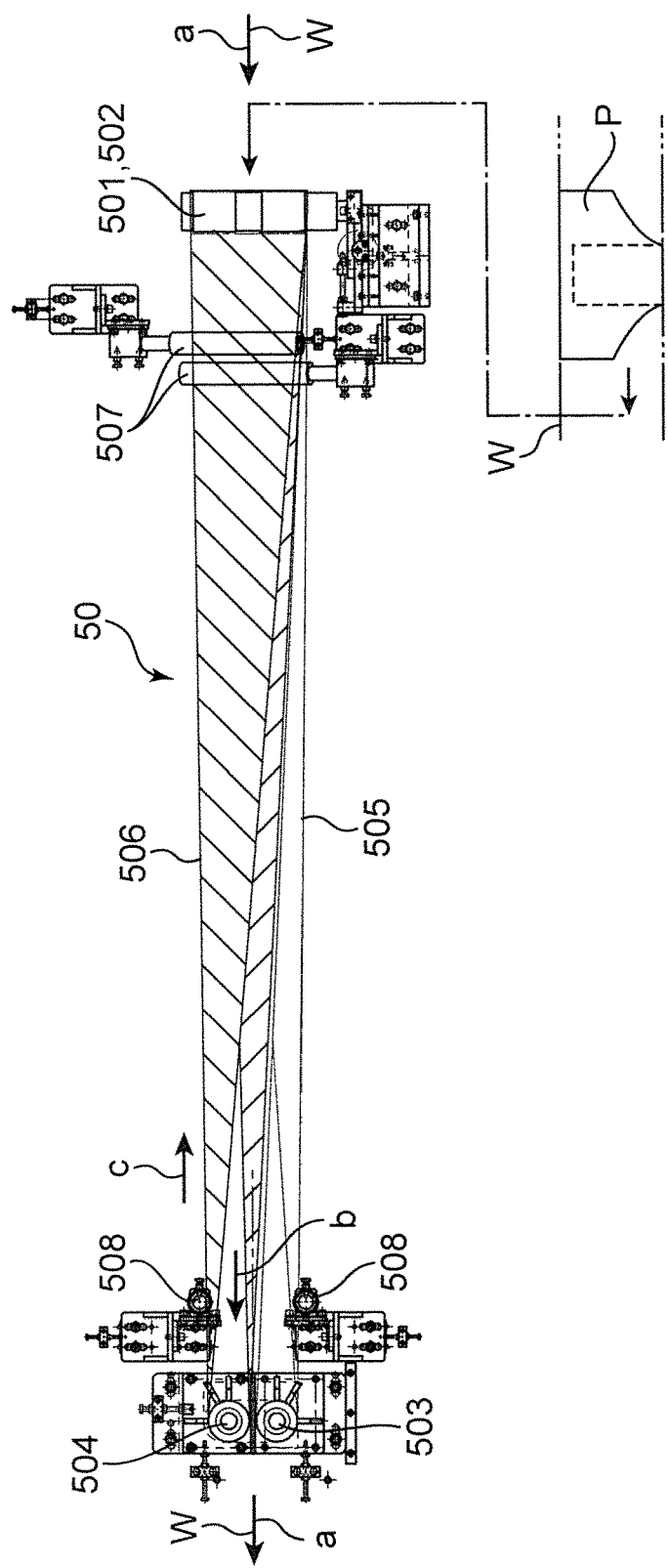
FIG. 4 is a plan view of a twisting unit in the device for producing a disposable wearable article according to the present invention.
Figure 5:
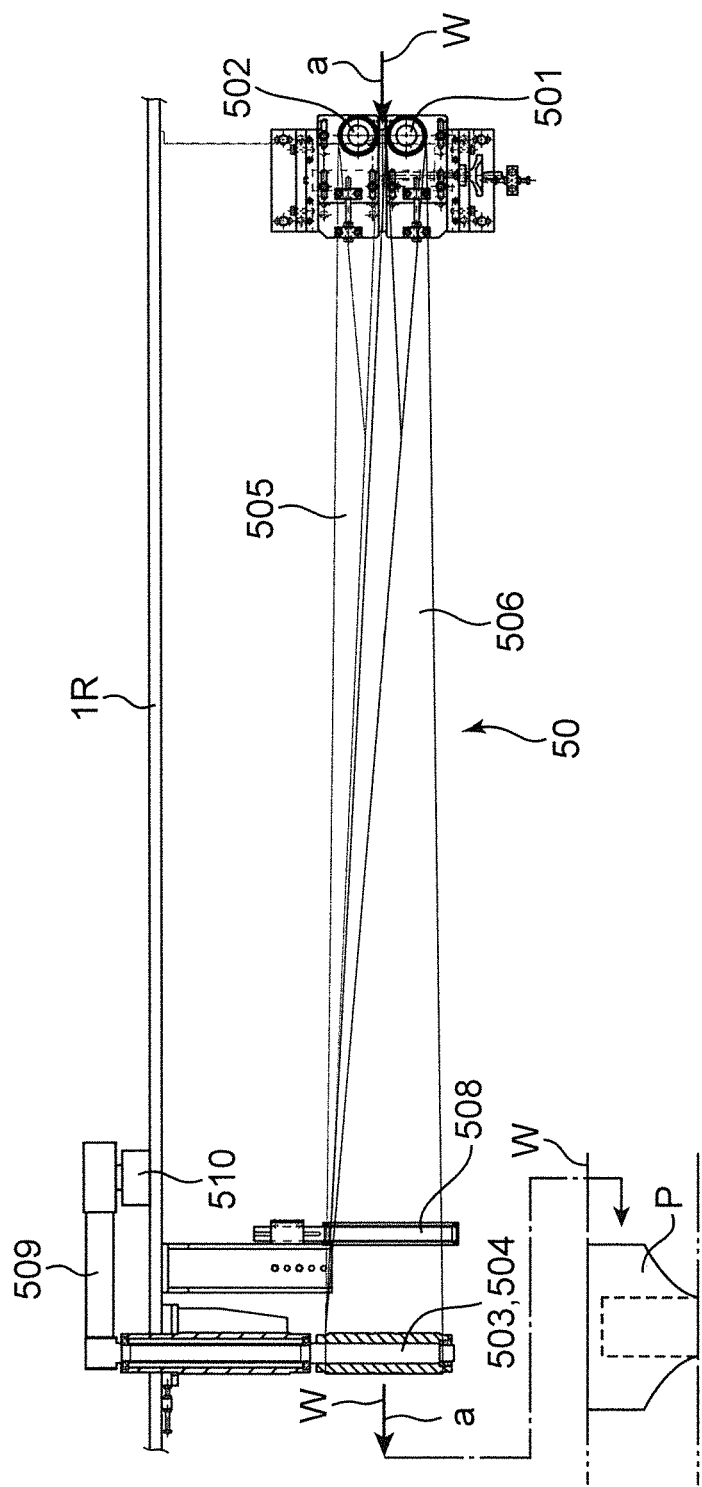
FIG. 5 is a side view of the twisting unit of FIG. 4.

Next, the specific configuration of the twisting unit 50 is described. FIG. 4 is a plan view of the twisting unit 50 and FIG. 5 is a side view of the twisting unit 50. A part of the sheet W, which will become the wearable article P, before the sheet W is carried to carry-in rollers 501, 502 is shown as a reference in FIG. 4. The part of the sheet W, which will become the wearable article P, after the sheet W is carried out from carry-out rollers 503, 504 is shown as a reference in FIG. 5.

In FIGS. 4 and 5, the sheet W doubled in the doubling unit 40 is conveyed from right to left while being continuously twisted from the vertical orientation to the horizontal orientation in the twisting unit 50.

The twisting unit 50 includes a pair of the carry-in rollers 501, 502 arranged on a carry-in side of the doubled sheet, a pair of the carry-out rollers 503, 504 arranged on a carry-out side, and a pair of twisting endless belts 505, 506.

The pair of carry-in rollers 501, 502 are arranged to be continuous with the carry-out side of the doubling unit 40 on the main support wall 1R, and the pair of carry-out rollers 503, 504 are arranged downstream of the carry-in rollers 501, 502 on the main supporting wall 1R.

The twisting endless belts 505, 506 have a width larger than that of the doubled sheet W and flat.

Further, the twisting endless belt 505 is mounted in a tense state between the carry-in roller 501 and the carry-out roller 503 facing each other, and the twisting endless belt 506 is mounted in a tense state between the carry-in roller 502 and the carry-out roller 504 facing each other. Parts of the pair of twisting endless belts 505, 506 facing each other are brought close to a substantially touching degree. Specifically, a clearance between the both twisting endless belts 505, 506 is set to be smaller than the sum of thicknesses of the doubled sheet W and the absorber C.

The pair of carry-in rollers 501, 502 on the carry-in side are vertically arranged and the pair of carry-out rollers 503, 504 on the carry-out side are horizontally arranged. This causes the respective twisting endless belts 505, 506 to be twisted 90° between the carry-in side and the carry-out side.

In FIG. 4, the twisting endless belt 506 between the carry-in roller 502 and the carry-out roller 504 is hatched to make a twisted state easily understandable. An arrow b facing leftward indicates a movement of the twisting endless belt 506 in a conveying direction and an arrow c facing rightward indicates a movement of the twisting endless belt 506 in a reverse conveying (returning) direction.

Regulating rollers 507, 508 for regulating the positions of the respective twisting endless belts 505, 506 are respectively provided near the pair of carry-in rollers 501, 502 on the carry-in side and the pair of carry-out rollers 503, 504 on the carry-out side.

Further, as shown in FIG. 5, the twisting unit 50 includes a twisting motor 510 for rotationally driving the carry-out rollers 503, 504 (driving the both twisting endless belts 505, 506) such that moving speeds of parts of the respective twisting endless belts 505, 506 for sandwiching the sheet W (parts facing each other) and the conveying speed of the sheet W are substantially equal.

Specifically, the twisting motor 510 is connected to pulleys (denoted by no reference sign) provided on the carry-out rollers 503, 504 via a timing belt 509.

According to the above twisting unit 50, the sheet W doubled to be in the vertical direction in the doubling unit 40 can be returned to the horizontal orientation, wherefore sealing is easily formed in a later process.

Figure 10:
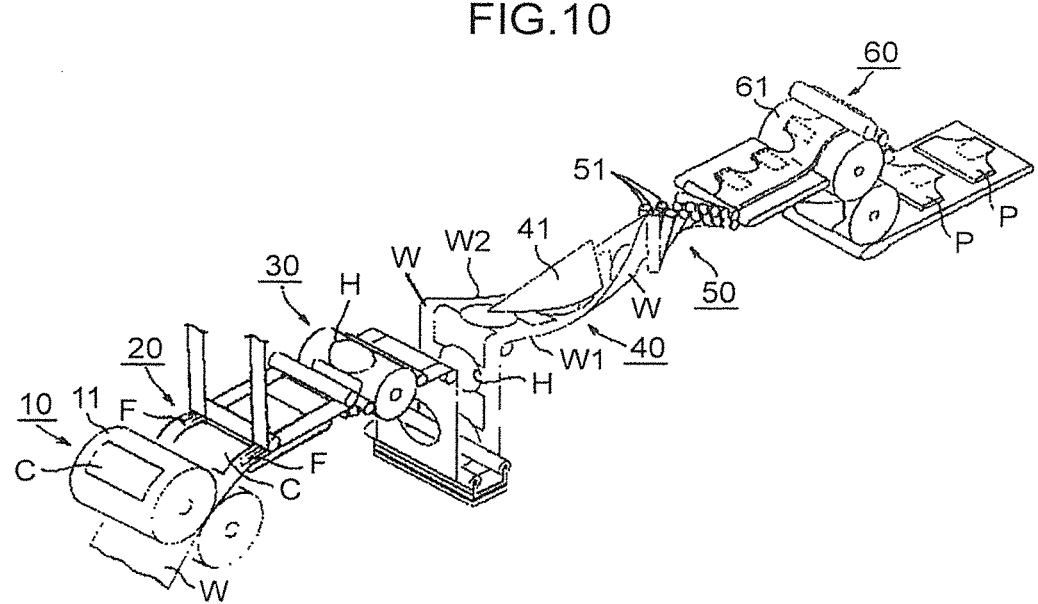
FIG. 10 is a perspective view of a device for producing a disposable wearable article according to a background art.

Further, in the conventional twisting unit 50 shown in FIG. 10, a plurality of guiding bars 51 arranged in two rows are used to twist the doubled sheet W from the vertical orientation to the horizontal orientation. In this case, since the sheet W is guided while being sandwiched between the rows of the plurality of guiding bars 51, the sheet W is held in point contact with each bar 51 in the twisting unit 50. Thus, if the conveying speed of the sheet W is increased, the conveying positions of the sheet W may be shifted to cause a trouble in a processing work in a process following that of the twisting unit.

In contrast, the above twisting unit 50 twists the sheet W 90° from the vertical orientation to the horizontal orientation by moving the sheet W together with the pair of twisting endless belts 505, 506 with the sheet W sandwiched from opposite sides by the twisting endless belts 505, 506. Thus, even if the conveying speed of the sheet W is increased, the conveying positions of the sheet W are not shifted and the occurrence of a trouble in a processing work in a process following the twisting process can be suppressed.

Further, the conventional twisting unit 50 shown in FIG. 10 requires a mechanism for allowing an increase of an interval between the two rows of the guiding bars 51 to softly sandwich the sheet W while absorbing the thickness of the absorber C and the like.

In contrast, since the twisting endless belts 505, 506 are deflectable between the carry-in rollers 501 502 and the carry-out rollers 503, 504 in the above twisting unit 50, the sheet W can be softly sandwiched while absorbing the thickness of the absorber C and the like. Thus, it is not necessary to specially provide a mechanism for allowing an increase of an interval between the twisting endless belts 505, 506.

Further, by moving the twisting endless belts 505, 506 by the twisting motor 510, the parts of the twisting endless belts 505 506 for sandwiching the sheet W move substantially at the same speed as the conveying speed of the sheet W, wherefore the sheet W and the absorber C can be smoothly conveyed at a high speed.

Furthermore, since the friction reducing mechanism (folding endless belt 408, etc.) is provided on the bottom edge of the doubling member 41 in the doubling unit 40 for performing the process before that of the twisting unit 50, friction can be reduced between the bottom edge of the doubling member 41 and the crotch part. Thus, a reduction of the conveying speed of the crotch part with respect to the conveying speed of the part of the sheet W other than the crotch part can be suppressed. Therefore, the sheet W can be conveyed at a high speed to the twisting unit 50 for performing the next process while being kept in a normal shape without distorting the shape of the sheet W in the conveying direction a. Also in the twisting unit 50, even if the conveying speed of the sheet W is increased, the conveying positions of the sheet W are not shifted and the occurrence of a trouble in the processing work in the next process can be suppressed. As just described, by combining the doubling unit 40 with the twisting unit 50, the conveying speed of the sheet W can be increased, wherefore the productivity of disposable wearable articles is improved.

Next, the specific configuration of the pressing unit 70 arranged upstream of the jointing/cutting unit 60 in the conveying direction a is described. Although the twisting unit 50 is provided between the doubling unit 40 and the jointing/cutting unit 60 in this embodiment, the pressing unit 70 can be provided between the doubling unit 40 and the jointing/cutting unit 60 in a producing device requiring no twisting unit 50.

Figure 6:
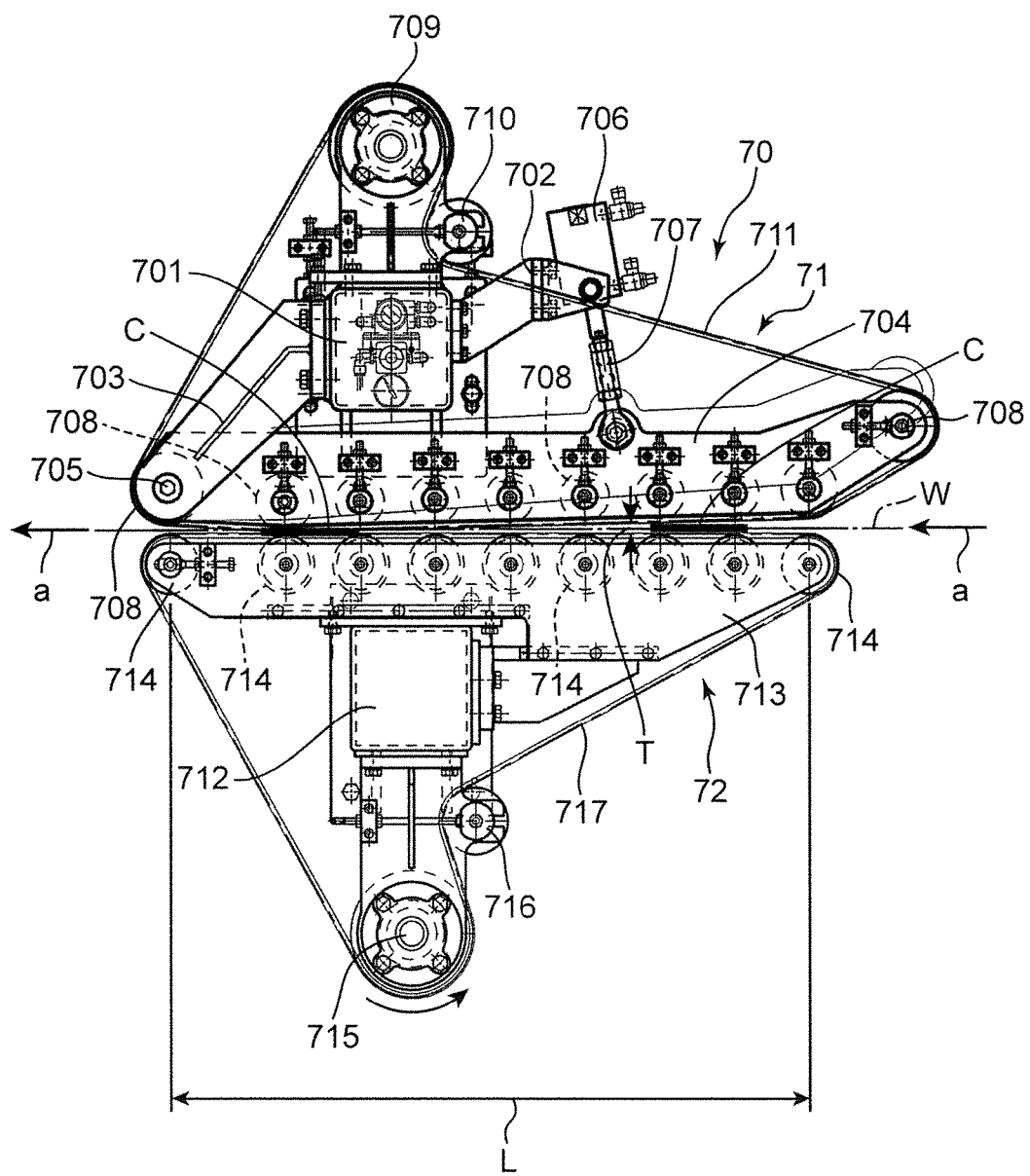
FIG. 6 is a side view of upper and lower pressing mechanisms of a pressing unit in the device for producing a disposable wearable article according to the present invention.

The pressing unit 70 includes pressing mechanisms for pressing the doubled sheet W together with the absorber C in a thickness direction. As shown in FIG. 6, the pressing mechanisms include an upper pressing mechanism 71 provided above the sheet W and a lower pressing mechanism 72 provided below the sheet W.

Figure 7A:
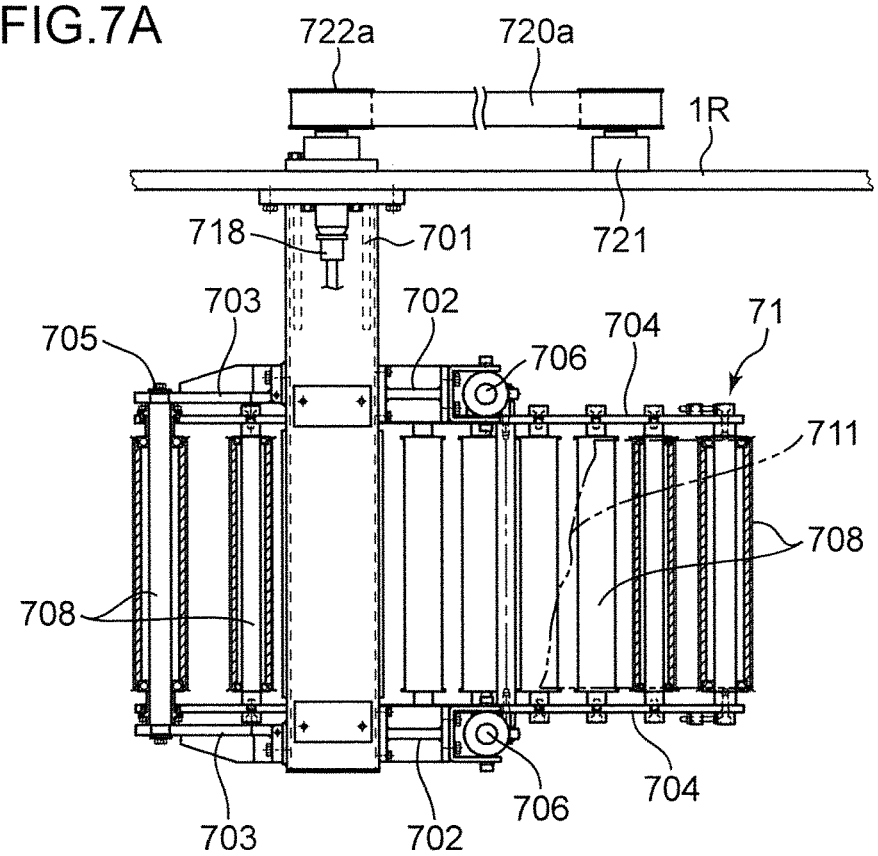
FIG. 7A is a plan view of the upper pressing mechanism.
Figure 7B:
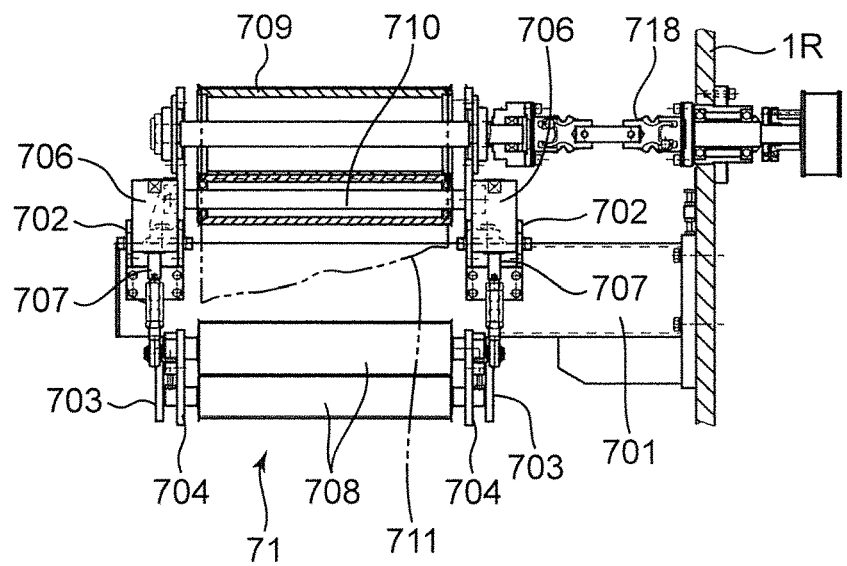
FIG. 7B is a front view in section of an essential part of the upper pressing mechanism.
Figure 8A:
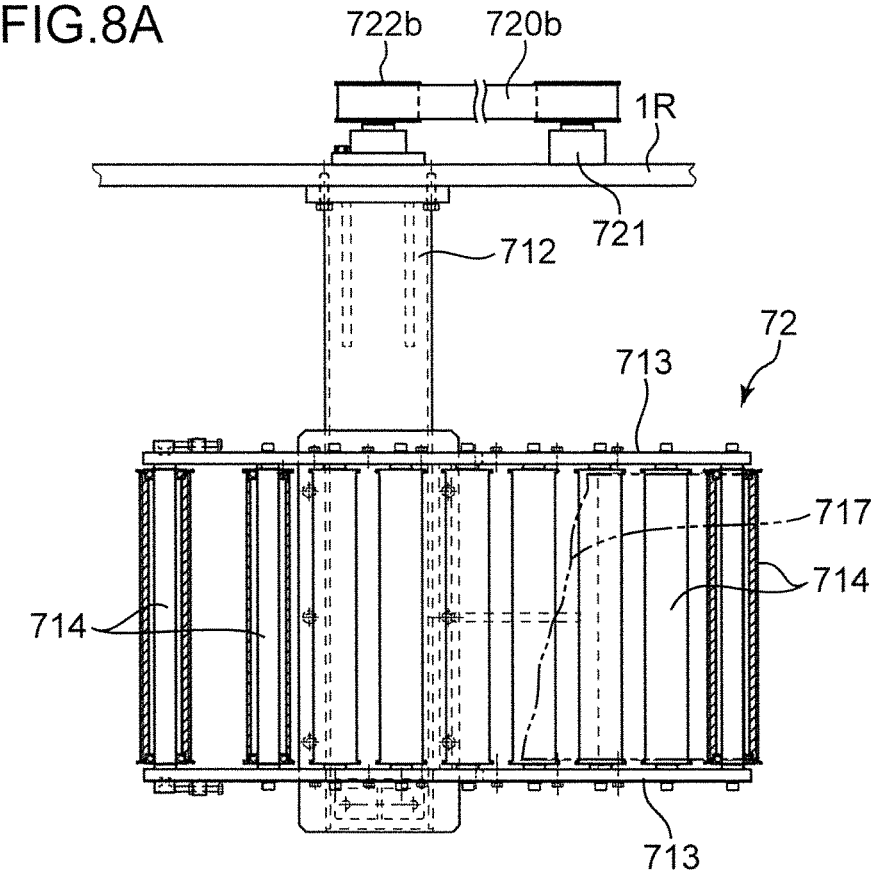
FIG. 8A is a plan view of the lower pressing mechanism.
Figure 8B:
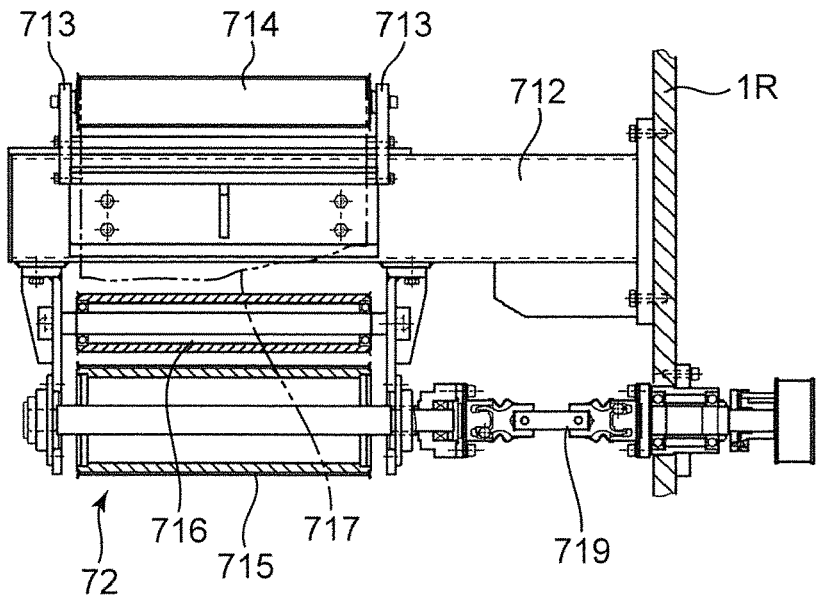
FIG. 8B is a front view in section of an essential part of the lower pressing mechanism.

FIG. 6 is a side view of the upper pressing mechanism 71 and the lower pressing mechanism 72 of the pressing unit. FIG. 7A is a plan view of the upper pressing mechanism 71 and FIG. 7B is a front view in section of an essential part of the upper pressing mechanism 71. FIG. 8A is a plan view of the lower pressing mechanism 72 and FIG. 8B is a front view in section of an essential part of the lower pressing mechanism 72.

In FIG. 6, the sheet W doubled in the doubling unit 40 and twisted to be in the horizontal orientation in the twisting unit 50 is continuously conveyed in the horizontal orientation from right to left.

The upper pressing mechanism 71 and the lower pressing mechanism 72 are arranged to be continuous with the carry-out side of the twisting unit 50 on the main supporting wall 1R while vertically facing each other.

As shown in FIGS. 7A and 7B, the upper pressing mechanism 71 includes a rectangular upper base box 701 projecting laterally from a side surface of the main supporting wall 1R. A pair of left and right upper base brackets 704 extending in the conveying direction a are provided on a pair of left and right brackets 703 on a carry-out side of this upper base box 701. Rear parts of the upper base brackets 704 are vertically swingably supported on the brackets 703 by a hinge shaft 705. Cylinders 706 are respectively supported on a pair of left and right brackets 702 on a carry-in side of the upper base box 701. Piston rods 707 of the respective cylinders 706 are coupled near intermediate parts of the respective upper base brackets 704.

A plurality of (ten in this example) upper rollers 708 are rotatably supported between the both upper base brackets 704 while being spaced at a predetermined interval in the conveying direction a. An upper main roller 709 and an upper tension roller 710 are rotatably supported on an upper part of the upper base box 701 via brackets (denoted by no reference signs).

A pressing endless belt 711 provided at one surface side (upper side) of the sheet W is mounted on each roller 708 to 710.

As shown in FIGS. 8A and 8B, the lower pressing mechanism 72 includes a rectangular lower base box 712 projecting laterally from the side surface of the main supporting wall 1R. A pair of left and right lower base brackets 713 extending in the conveying direction a are provided on an upper part of this lower base box 712.

A plurality of (nine in this example) lower rollers 714 are rotatably supported between the both lower base brackets 713 while being spaced at a predetermined interval in the conveying direction a. A lower main roller 715 and a lower tension roller 716 are rotatably supported on a lower part of the lower base box 712 via brackets (denoted by no reference signs).

A pressing endless belt 717 provided at the opposite surface side (lower side) of the sheet W is mounted on each roller 714 to 716.

That is, the base brackets 704, 713 and the rollers 708 to 710, 714 to 716 correspond to a holding mechanism for holding the pair of pressing endless belts 711, 714 such that parts of the pair of pressing endless belts 711, 717 for pressing the sheet W are movable in the conveying direction a.

Further, by driving the cylinders 706 of the upper pressing mechanism 71, the upper base brackets 704 rotate about the hinge shaft 705 and the pressing endless belt 711 of the pressing mechanism 71 moves toward or away from the pressing endless belt 717 of the lower pressing mechanism 72.

That is, the hinge shaft 705 and the cylinders 706 correspond to a supporting mechanism for supporting the holding mechanism such that the pressing endless belt 711 is movable toward and away from the pressing endless belt 717.

Note that, instead of the upper pressing mechanism 71, the lower pressing mechanism 72 may be provided with a supporting mechanism or both upper and lower pressing mechanisms 71, 72 may be provided with supporting mechanisms.

A width of each pressing endless belt 711, 717 is set to be larger than the width of the doubled sheet W.

As shown in FIGS. 7A and 7B, a rotary shaft of the upper main roller 709 is coupled to a timing pulley 722a arranged on an outer side of the main supporting wall 1R via an upper joint 718. Similarly, as shown in FIGS. 8A and 8B, a rotary shaft of the lower main roller 715 is coupled to a timing pulley 722b arranged on the outer side of the main supporting wall 1R via an lower joint 719. Pressing motors 721 (see FIGS. 7A and 8A) are coupled to these timing pulleys 722a, 722b via timing belts 720a, 720b. By driving the pressing motors 721, the upper main roller 709 and the lower main roller 715 are respectively synchronously rotated in a clockwise direction and a counterclockwise direction of FIG. 6 via the timing belts 720a, 720b.

That is, the pressing motors 721 drive the both pressing endless belts 711, 717 such moving speeds of the parts of the respective pressing endless belts 711, 717 facing each other (parts for pressing the sheet W) and the conveying speed of the sheet W are substantially equal.

The part of the pressing endless belt 711 of the upper pressing mechanism 71 facing the pressing endless belt 717 is inclined downwardly toward a downstream side in the conveying direction a. Further, a minimum clearance T between the parts of the both pressing endless belts 711, 717 for pressing the sheet W is set to be smaller than the sum of the thicknesses of the doubled sheet W and the absorber C.

Further, lengths L of the parts of the respective pressing endless belts 711, 717 for pressing the absorber C together with the sheet W are set at a length longer than the arrangement interval of the absorbers C on the sheet W, more preferably the sum of that arrangement interval and a length longer than a length of the absorber C in the conveying direction a. Note that, in this embodiment, the length L corresponds to a distance from a center of the lower roller 714 arranged on a foremost side of the lower pressing mechanism 72 to a center of the lower roller 714 arranged on a rearmost side as shown in FIG. 6. Note that the length L is appropriately set according to the interval of the absorbers C.

The pressing unit 70 presses the doubled sheet W together with the absorber C in the thickness direction between the pressing endless belt 711 of the upper pressing mechanism 71 and the pressing endless belt 717 of the lower pressing mechanism 72.

According to the pressing unit 70, the pressing mechanisms 71, 72 are provided to sandwich and press the doubled sheet W together with the absorber C in the thickness direction while conveying the sheet W. This makes it difficult for the doubled sheet W to open against an elastic force of the absorber C. Thus, the sheet W on one side, which will become a front belly part, and the sheet W on the other side, which will become a back part, are held in a state of adhesion in joined (sealed) parts at the opposite sides of the absorber C later in the joining/cutting unit 60, wherefore the occurrence of a sealing failure can be suppressed. Here, joining (sealing) is not limited to thermal welding and may be hot melt adhesion. Further, since the doubled sheet W can be sandwiched and pressed together with the absorber C in the thickness direction while being conveyed, the sheet W can be conveyed at a high speed to the next process.

Further, if not being moved by the pressing motors 721, the pressing endless belts 711, 717 can move together with the sheet W in the conveying direction a due to a contact friction force of the parts sandwiching the absorber C of the sheet W (absorber C parts). Also in this case, the pressing endless belts 711, 717 can press the sheet W together with the absorber C in the thickness direction while smoothly conveying the sheet W and the absorber C.

Further, the lengths L of the parts of the respective pressing endless belts 711, 717 for pressing the absorber C together with the sheet W are set at the length longer than the arrangement interval of the absorbers C on the sheet W. Thus, at least one absorber C is sandwiched between the parts of the respective pressing endless belts 711, 717 for pressing the absorber C together with the sheet W, thereby being able to prevent only the sheet W part between the absorbers C adjacent in the front-back direction from being sandwiched between these pressing parts. Therefore, the part of the sheet W including the absorber C is sandwiched by a constant pressing force and it can be suppressed that only the sheet W is sandwiched and the sheet W is shifted.

Furthermore, since the upper pressing mechanism 71 is provided with the supporting mechanism (hinge shaft 705 and cylinders 706), the minimum clearance T between the upper and lower pressing endless belts 711, 717 can be finely adjusted by the driving of the cylinders 706. This enables the sheet W to be pressed together with the absorber C with a predetermined pressing force. Further, when a leader part of the sheet W is passed through the clearance before the line L1 is driven, the minimum clearance T can be expanded by the cylinders 706, wherefore an operation of passing the leader part is facilitated.

Further, by moving the pressing endless belts 711, 717 by the pressing motors 721, the parts of the pressing endless belts 711, 717 for pressing the sheet W move substantially at the same speed as the conveying speed of the sheet W, wherefore the absorber C can be smoothly conveyed together with the sheet W at a high speed.

A method for producing a disposable wearable article using the device for producing a disposable wearable article described above is described with reference to FIG. 9.

This producing method includes a conveying process, an absorber arranging process, an elastic attaching process, a hole forming process, a doubling process, a twisting process, a pressing process and a joining/cutting process.

In the conveying process, the sheet W is continuously conveyed along the line L1.

In the absorber arranging process, the absorbers C are intermittently arranged on the surface of the sheet W.

In the elastic attaching process, the waist elastic F is attached to the surface of the sheet W.

In the hole forming process, the holes H, which will become leg holes, are formed at the positions of the sheet W at the opposite sides of the absorber C.

In the doubling process, the sheet W is doubled together with the absorber C such that the opposite side edges W1, W2 of the sheet W having the absorber C thereon are proximate to or overlapped with each other. Further, in the doubling process, the sheet W is doubled such that the sheet W conveyed in the horizontal orientation is arranged in the vertical orientation. Specifically, in the doubling process, the sheet W is doubled using the doubling member 41 including the aforementioned friction reducing mechanism.

In the twisting process, the sheet W arranged in the vertical orientation in the doubling process is twisted (returned). Further, in the twisting process, the sheet W is twisted while being conveyed with the sheet W sandwiched between the twisting endless belts 505, 506.

In the pressing process, the doubled sheet W is pressed together with the absorber C in the thickness direction prior to the joining/cutting process.

In the joining/cutting process, after the parts of the doubled sheet W at the opposite sides of the absorber C are joined, these joined parts are cut.

Note that the specific embodiment described above mainly includes inventions having the following configurations.

Specifically, the present invention provides a device for producing a disposable wearable article, the device including a doubling unit provided in a line for continuously conveying a sheet and configured to double the sheet together with an absorber such that opposite side edges of the sheet having the absorber arranged thereon are proximate to or overlapped with each other, a joining/cutting unit provided in the line and configured to join parts of the doubled sheet at opposite sides of the absorber and then cut the joined parts and a pressing unit arranged upstream of the joining/cutting unit in a sheet conveying direction, the pressing unit including a pressing mechanism configured to press the doubled sheet together with the absorber in a thickness direction.

According to the present invention, the doubled sheet is made difficult to open against an elastic force of the absorber by providing the pressing mechanism configured to sandwich and press the doubled sheet together with the absorber in the thickness direction while conveying the sheet. Thus, the sheet on one side, which will become a front belly part, and the sheet on the other side, which will become a back part, are held in a state of adhesion in the joined (sealed) parts at the opposite sides of the absorber later in the joining/cutting unit, wherefore the occurrence of a sealing failure can be suppressed. Further, since the doubled sheet can be sandwiched and pressed together with the absorber in the thickness direction while being conveyed, the sheet can be conveyed at a high speed to the next process.

In the above device for producing a disposable wearable article, preferably, the pressing mechanism includes a pair of pressing endless belts respectively provided at one surface side and the other surface side of the doubled sheet and each having a part for pressing the sheet and a holding mechanism configured to hold the pair of pressing endless belts such that the parts of the pair of pressing endless belts for pressing the sheet are movable in the conveying direction, and a minimum clearance between the parts of the both pressing endless belts for pressing the sheet is set to be not larger than the sum of thicknesses of the doubled sheet and the absorber.

According to this configuration, the pressing endless belts are movable together with the sheet in the conveying direction due to a friction force generated when a part of the sheet where the absorber is arranged comes into contact with the pressing endless belts. Thus, the pressing endless belts can press the sheet together with the absorber in the thickness direction while smoothly conveying the sheet and the absorber.

In the above device for producing a disposable wearable article, lengths of the parts of the pressing endless belts for pressing the sheet are preferably set at a length not shorter than an arrangement interval of the absorbers on the sheet, more preferably set at a length not shorter than the sum of the arrangement interval and a length of the absorber in the conveying direction.

According to this configuration, at least one absorber is sandwiched between the parts of the both pressing endless belts for pressing the absorber together with the sheet, thereby being able to prevent only the sheet part between the absorbers adjacent in a front-back direction from being sandwiched between these pressing parts. Thus, the part of the sheet including the absorber is sandwiched by a constant pressing force and it can be suppressed that only the sheet is sandwiched and the sheet is shifted.

In the above device for producing a disposable wearable article, the pressing mechanism preferably further includes a supporting mechanism configured to support the holding mechanism such that one of the both pressing endless belts is movable toward and away from the other.

According to this configuration, the clearance between the both pressing endless belts can be adjusted by the supporting mechanism (e.g. by driving a cylinder in the case of providing the cylinder as the supporting mechanism). This enables the sheet to be pressed together with the absorber with a predetermined pressing force. Further, when a leader part of the sheet is passed through the clearance before the line is driven, the clearance can be expanded by the supporting mechanism, wherefore an operation of passing the leader part is facilitated.

In the above device for producing a disposable wearable article, the pressing mechanism preferably further includes a pressing motor configured to drive the both pressing endless belts such that moving speeds of the parts of the both pressing endless belts for pressing the sheet and a conveying speed of the sheet are substantially equal.

According to this configuration, since the parts of the both pressing endless belts for pressing the sheet move substantially at the same speed as the conveying speed of the sheet by moving the pressing endless belts by the pressing motor, the absorber can be smoothly conveyed together with the sheet at a high speed.

Here, in the device for producing a disposable wearable article of patent literature 1 (see FIG. 10), the doubling member 41 of the doubling unit 40 is formed of a plate member made of metal and having a bottom edge curved in the conveying direction. In the case of pressing the thick absorber C against the bottom edge of this doubling member 41, friction is generated between the crotch part of the sheet W including the absorber and the doubling member 41. A conveying timing of the crotch part may be delayed with respect to a part of the sheet W other than the crotch part due to this friction. Thus, there is a problem of distorting the shape of the sheet W in the conveying direction and conveying the sheet W in that distorted state to the next process.

Accordingly, in the above device for producing a disposable wearable article, preferably, the doubling unit includes a doubling member having a bottom edge for doubling the sheet, and the doubling member includes a friction reducing mechanism provided on the bottom edge and configured to reduce friction between the doubling member and a crotch part of the sheet including the absorber in a state held in contact with the crotch part.

According to this configuration, the doubling unit includes the friction reducing mechanism provided on the bottom edge of the doubling member. This enables the friction between the bottom edge of the doubling member and the crotch part to be reduced. Thus, a reduction of a conveying speed of the crotch part with respect to a part of the sheet W other than the crotch part can be suppressed. Thus, the sheet can be conveyed at a high speed to the next process while being kept in a normal shape without distorting the shape of the sheet in the conveying direction. As a result, the occurrence of a trouble in a processing work in a process succeeding a doubling process can be suppressed.

Here, the friction reducing mechanism may include a plurality of rotatable rollers arranged side by side on the bottom edge of the doubling member.

According to this configuration, the friction between the crotch part and the doubling member is reduced by the free rotation of the rollers.

In the above device for producing a disposable wearable article, preferably, the friction reducing mechanism includes a plurality of pulleys rotatably provided on the bottom edge of the doubling member and a folding endless belt mounted on each pulley, and the plurality of pulleys hold the folding endless belt such that a part of the folding endless belt in contact with the crotch part is movable in the sheet conveying direction.

According to this configuration, the folding endless belt is movable together with the sheet in the conveying direction, accompanying the rotation of the pulleys, due to a friction force generated when the crotch part comes into contact with the folding endless belt. Thus, friction between the folding endless belt and the crotch part can be reduced.

In the above device for producing a disposable wearable article, the friction reducing mechanism preferably further includes a folding motor configured to drive the folding endless belt such that a moving speed of a part of the folding endless belt in contact with the crotch part and the conveying speed of the sheet are substantially equal.

According to this configuration, the folding endless belt moves substantially at the same speed as the conveying speed of the sheet by moving the folding endless belt by the folding motor, wherefore friction between the folding endless belt and the crotch part can be completely or mostly eliminated.

In the above device for producing a disposable wearable article, the doubling unit preferably further includes a posture adjusting mechanism provided on a side surface part of the doubling member and capable of adjusting the posture of the sheet by coming into contact with an inner surface of the sheet being doubled.

According to this configuration, the since the posture of the sheet can be adjusted by the posture adjusting mechanism, it is possible to easily and quickly finely adjust the posture of the sheet unlike a conventional doubling member formed of a metal plate material with which the posture of the sheet cannot be adjusted unless the doubling member is exchanged.

Further, unlike a case where the sheet is suddenly doubled in the conveying direction, the sheet can be gradually doubled by the posture adjusting mechanism, wherefore tension generated on an edge part of the sheet in a width direction can be alleviated.

Here, in the doubling unit 50 of the device for producing a disposable wearable article of patent literature 1 (see FIG. 10), a plurality of guiding bars 51 arranged in two rows are used to twist the doubled sheet W from the vertical orientation to the horizontal orientation. In this case, since the sheet W is guided while being sandwiched between the rows of the plurality of guiding bars 51, the sheet W is held in point contact with each guiding bar 51 in the twisting unit 50. Thus, if the conveying speed of the sheet W is increased, there is a problem that the conveying positions of the sheet W may be shifted to cause a trouble in a processing work in a process following the twisting process.

Accordingly, preferably, the above device for producing a disposable wearable article further includes a twisting unit provided in the line and configured to twist the sheet doubled by the doubling unit from a vertical orientation to a horizontal orientation, the twisting unit includes a pair of carry-in rollers arranged on a carry-in side of the doubled sheet, a pair of carry-out rollers arranged on a carry-out side and a pair of twisting endless belts each mounted between the carry-in roller and the carry-out roller facing each other, the pair of carry-in rollers are vertically arranged and the pair of carry-out rollers are horizontally arranged such that each twisting endless belt is twisted about 90° between the carry-in side and the carry-out side.

According to this configuration, since the sheet doubled to be in the vertical orientation in the doubling unit can be returned to the horizontal orientation in the twisting unit, sealing is easily performed in a later process.

Further, the twisting unit of the present invention twists the sheet 90° from the vertical orientation to the horizontal orientation by moving the sheet together with the pair of twisting endless belts with the sheet sandwiched from opposite sides by the twisting endless belts. Thus, even if the conveying speed of the sheet is increased, the conveying positions of the sheet are not shifted and the occurrence of a trouble in a processing work in a process following the twisting process can be suppressed.

Further, the conventional twisting unit requires a mechanism for allowing an increase of an interval between two rows of the guiding bars to softly sandwich the sheet while absorbing a thickness of the absorber and the like.

In contrast, since the twisting endless belts are deflectable between the carry-in rollers and the carry-out rollers in the above twisting unit, the sheet can be softly sandwiched while absorbing a thickness of the absorber and the like. Thus, it is not necessary to specially provide the mechanism for allowing an increase of an interval between the twisting endless belts.

Note that, in the above configuration, the "carry-in roller and carry-out roller facing each other" means the rollers located on the same side with respect to the sheet.

In the above device for producing a disposable wearable article, the twisting unit preferably further includes a twisting motor configured to drive the both twisting endless belts such that moving speeds of parts of the both twisting endless belts for sandwiching the sheet and the conveying speed of the sheet are substantially equal.

According to this configuration, since the twisting endless belts move substantially at the same speed as the conveying speed of the sheet by moving the twisting endless belts by the twisting motor, the sheet and the absorber can be smoothly conveyed at a high speed.

Note that, according to the configuration with the aforementioned doubling unit including the friction reducing mechanism and the aforementioned doubling unit, the following effects can be exhibited.

Since the friction reducing mechanism is provided on the bottom edge of the doubling member in the doubling unit for performing the process preceding that of the twisting unit, friction between the bottom edge of the doubling member and the crotch part can be reduced. Accordingly, a reduction of the conveying speed of the crotch part with respect to the part of the sheet W other than the crotch part can be suppressed. Thus, the sheet can be conveyed at a high speed to the next process while being kept in a normal shape without distorting the shape of the sheet in the conveying direction. Also in the twisting unit, even if the conveying speed of the sheet is increased, the conveying positions of the sheet are not shifted and the occurrence of a trouble in the processing work in the next process can be suppressed. As just described, since the conveying speed of the sheet can be increased by combining the doubling unit including the friction reducing mechanism with the twisting unit, the productivity of disposable wearable articles is improved.

Further, the present invention provides a method for producing a disposable wearable article, the method including a conveying process of continuously conveying a sheet, an absorber arranging process of arranging an absorber on a surface of the sheet, a doubling process of doubling the sheet together with the absorber such that opposite side edges of the sheet having the absorber arranged thereon are proximate to or overlapped with each other, a jointing/cutting process of joining parts of the doubled sheet at opposite sides of the absorber and then cutting the joined parts and a pressing process of pressing the doubled sheet together with the absorber prior to the jointing/cutting process.

According to the present invention, the doubled sheet is made difficult to open against an elastic force of the absorber by sandwiching and pressing the sheet together with the absorber in a thickness direction while conveying the sheet. Thus, the sheet on one side, which will become a front belly part, and the sheet on the other side, which will become a back part, are held in a state of adhesion in the joined (sealed) parts at the opposite sides of the absorber later in the joining/cutting process, wherefore the occurrence of a sealing failure can be suppressed. Further, since the doubled sheet can be sandwiched and pressed together with the absorber in the thickness direction while being conveyed, the sheet can be conveyed at a high speed to the next process.

The invention claimed is:

1. A device for producing a disposable wearable article, comprising:
    a doubling unit provided in a line for continuously conveying a sheet and configured to double the sheet together with an absorber such that opposite side edges of the sheet having the absorber arranged thereon are proximate to or overlapped with each other;
    a joining/cutting unit provided in the line and configured to join parts of the doubled sheet at opposite sides of the absorber and then cut the joined part; and
    a pressing unit arranged upstream of the joining/cutting unit in a sheet conveying direction, the pressing unit including a pressing mechanism configured to press the doubled sheet together with the absorber in a thickness direction, wherein:
    the pressing mechanism includes a pair of pressing endless belts respectively provided at one surface side and the other surface side of the doubled sheet and each having a part for pressing the sheet and a holding mechanism configured to hold the pair of pressing endless belts such that the parts of the pair of pressing endless belts for pressing the sheet are movable in the sheet conveying direction;

a minimum clearance between the parts of the pressing endless belts for pressing the sheet is set to be not larger than the sum of thicknesses of the doubled sheet and the absorber;

lengths of the parts of the pressing endless belts for pressing the sheet are set at a length not shorter than an arrangement interval of the absorbers on the sheet; and one in the pair of pressing endless belts comprises a first inclined part inclined toward the other in the pair of pressing endless belts side from an upstream end to downstream of the one pressing endless belt in the sheet conveying direction and a second inclined part inclined toward the other pressing endless belt side from a downstream end of the first inclined part to a point where a clearance between the parts of the pressing endless belts for pressing the sheet is set to a minimum value, and an inclination angle of the second inclined part with respect to the other pressing endless belt is smaller than that of the first inclined part.

2. A device for producing a disposable wearable article according to claim 1, wherein:

the pressing mechanism further includes a supporting mechanism configured to support the holding mechanism such that one of the both pressing endless belts is movable toward and away from the other.

3. A device for producing a disposable wearable article according to claim 1, wherein:

the pressing mechanism further includes a pressing motor configured to drive the both pressing endless belts such that moving speeds of the parts of the both pressing endless belts for pressing the sheet and a conveying speed of the sheet are substantially equal.

4. The device for producing a disposable wearable article according to claim 1, wherein:

the doubling unit includes a doubling member having a bottom edge for doubling the sheet; and the doubling member includes a friction reducing mechanism provided on the bottom edge and configured to reduce friction between the doubling member and a crotch part of the sheet including the absorber in a state held in contact with the crotch part.

5. The device for producing a disposable wearable article according to claim 4, wherein:

the friction reducing mechanism includes a plurality of pulleys rotatably provided on the bottom edge of the doubling member and a folding endless belt mounted on each pulley; and the plurality of pulleys hold the folding endless belt such that a part of the folding endless belt in contact with the crotch part is movable in the sheet conveying direction.

6. The device for producing a disposable wearable article according to claim 5, wherein:

the friction reducing mechanism further includes a folding motor configured to drive the folding endless belt such that a moving speed of the part of the folding endless belt in contact with the crotch part and the conveying speed of the sheet are substantially equal.

7. The device for producing a disposable wearable article according to claim 4, wherein:

the doubling unit further includes a posture adjusting mechanism provided on a side surface part of the doubling member and capable of adjusting the posture of the sheet by coming into contact with an inner surface of the sheet being doubled.

8. The device for producing a disposable wearable article according to claim 1, further comprising a twisting unit provided in the line and configured to twist the sheet doubled by the doubling unit from a vertical orientation to a horizontal orientation, wherein:

the twisting unit includes a pair of carry-in rollers arranged on a carry-in side of the doubled sheet, a pair of carry-out rollers arranged on a carry-out side and a pair of twisting endless belts each mounted between the carry-in roller and the carry-out roller facing each other; and the pair of carry-in rollers are vertically arranged and the pair of carry-out rollers are horizontally arranged such that each twisting endless belt is twisted about 90□ between the carry-in side and the carry-out side.

9. The device for producing a disposable wearable article according to claim 8, wherein:

the twisting unit further includes a twisting motor configured to drive the both twisting endless belts such that moving speeds of parts of the both twisting endless belts for sandwiching the sheet and the conveying speed of the sheet are substantially equal.

10. A device for producing a disposable wearable article, comprising:

pulleys provided in a line and carrying a folding endless belt for continuously conveying a sheet and configured to double the sheet together with an absorber such that opposite side edges of the sheet having the absorber arranged thereon are proximate to or overlapped with each other;

a drum provided in the line and configured to join parts of the doubled sheet at opposite sides of the absorber and then cut the joined part; and a pressing unit arranged upstream of the drum in a sheet conveying direction, the pressing unit including a pressing mechanism configured to press the doubled sheet together with the absorber in a thickness direction, wherein:

the pressing mechanism includes a pair of pressing endless belts respectively provided at one surface side and the other surface side of the doubled sheet and each having a part for pressing the sheet and a holding mechanism configured to hold the pair of pressing endless belts such that the parts of the pair of pressing endless belts for pressing the sheet are movable in the sheet conveying direction;

a minimum clearance between the parts of the pressing endless belts for pressing the sheet is set to be not larger than the sum of thicknesses of the doubled sheet and the absorber;

lengths of the parts of the pressing endless belts for pressing the sheet are set at a length not shorter than an arrangement interval of the absorbers on the sheet; and one in the pair of pressing endless belts comprises a first inclined part inclined toward the other in the pair of pressing endless belts side from an upstream end to downstream of the one pressing endless belt in the sheet conveying direction and a second inclined part inclined toward the other pressing endless belt side from a downstream end of the first inclined part to a point where a clearance between the parts of the pressing endless belts for pressing the sheet is set to a minimum value, and an inclination angle of the second inclined part with respect to the other pressing endless belt is smaller than that of the first inclined part.

\* \* \* \* \*